United States Patent [19]

Suga

[11] Patent Number: 5,138,892

[45] Date of Patent: Aug. 18, 1992

[54] ACCELERATED LIGHT FASTNESS TEST METHOD

[75] Inventor: Shigeru Suga, Tokyo, Japan

[73] Assignee: Suga Test Instruments Co., Ltd., Tokyo, Japan

[21] Appl. No.: 524,049

[22] Filed: May 16, 1990

[30] Foreign Application Priority Data

Aug. 17, 1989 [JP] Japan .................. 1-211639

[51] Int. Cl.$^5$ .................................. G01N 17/00
[52] U.S. Cl. .......................... 73/865.6; 374/57
[58] Field of Search ............... 73/865.6; 374/57

[56] References Cited

U.S. PATENT DOCUMENTS

| | | | |
|---|---|---|---|
| 2,523,322 | 9/1950 | Ornstein et al. | 374/57 |
| 3,576,125 | 4/1971 | Kockott et al. | 374/57 |
| 3,797,918 | 3/1974 | Kockott | 73/865.6 X |
| 4,627,287 | 12/1986 | Suga | 73/865.6 |
| 4,634,290 | 1/1987 | Roencwaig et al. | 374/57 X |
| 4,706,903 | 11/1987 | Suga et al. | 73/865.6 X |
| 4,760,748 | 8/1988 | Katayanagi et al. | 374/57 X |
| 4,807,247 | 2/1989 | Robbins, III | 374/57 |
| 4,817,447 | 4/1989 | Kashima et al. | 73/865.6 |
| 4,995,273 | 2/1991 | Kisima et al. | 73/865.6 |

FOREIGN PATENT DOCUMENTS

| | | | |
|---|---|---|---|
| 544 | 1/1982 | Japan | 73/865.6 |
| 14740 | 1/1982 | Japan | 73/865.6 |
| 32847 | 2/1984 | Japan | 374/57 |
| 117128 | 6/1985 | Japan | 374/57 |
| 61935 | 3/1988 | Japan | 374/57 |
| 746208 | 7/1980 | U.S.S.R. | 374/57 |

OTHER PUBLICATIONS

*Patent Abstracts of Japan;* Grp. p. 971, vol. 13, No. 547, Abs. Pub. Date Dec. 7, 1989 (01-227944).
*Patent Abstracts of Japan;* Grp. p. 282, vol. 8, No. 137, Abs. Pub. Date Jun. 26, 1984 (59-37446).

*Primary Examiner*—Tom Noland
*Attorney, Agent, or Firm*—Wenderoth, Lind & Ponack

[57] ABSTRACT

A method of carrying out an accelerated light fastness test on a sample of a material to be used under certain conditions of air convection along the surface thereof, is constituted by the steps of positioning a sample to be tested with the surface thereof which is exposed to light during intended conditions of use of the material spaced at a distance from a light source having a constant intensity of light radiated therefrom for causing the surface of the sample to receive a desired intensity of light, and positioning a filter between the surface of the sample and the light source and spaced a distance from the surface of the sample for causing air between the filter and the sample to be at the convection conditions corresponding to the certain conditions of air convection at the surface of the material under its intended conditions of use, whereby the temperature conditions of the material at the surface facing the source of light are made to correspond to the temperature conditions during the intended use of the material.

1 Claim, 4 Drawing Sheets

ACCELERATED LIGHT FASTNESS TEST METHOD

This invention relates to a method of regulating the temperature of the surface of a sample in a light fastness test machine for conducting an accelerated light fastness test, i.e. a test for determining the deterioration of a paint film, or a material such as fiber or plastic, or any product when exposed to sunlight.

BACKGROUND OF THE INVENTION

The purpose of an accelerated light fastness test is to reproduce in a laboratory in a short period of time the conditions under which a sample is deteriorated outdoors by the synergetic effect of sunlight and solar heat, and accurately estimate the lifetime of the sample. To achieve this purpose, a test method of irradiating a sample with light at a predetermined light intensity from a light source provided in a test chamber and having a spectral distribution similar to that of sunlight, and maintaining the temperature of the sample at a predetermined temperature has been employed.

FIG. 6 is a schematic sectional side elevation of a conventional accelerated light fastness test machine 7 in which an example of such a method is used. This apparatus is provided in a test chamber 8 with a xenon lamp 5 as a light source for emitting light of a predetermined intensity, and with a circular sample holder frame 4 adapted to be rotated around the light source 5. Sample holders 1' on which samples 2 are mounted, and black panel thermometers 6 for ascertaining the test temperature are supported on this sample holder frame 4. Outside air is introduced into the test chamber 8 by a blower 9, the air being circulated therein and discharged therefrom to make the temperature distribution in the test chamber 8 and the surface temperatures of the samples 2 and black panel thermometers 6 uniform. The rate of introduction of the outside air and the rate of discharge of the air in the test chamber 8 are regulated by suitably displacing a damper 10 in accordance with the output from a temperature sensor (not shown) provided in the test chamber 8, and the outside air is heated as necessary by a heater 11.

The surface temperature of the samples is influenced by the radiant heat from the light source 5, the temperature of the air in the test chamber 8, the material and color of the samples and the heat radiated from the surfaces of the samples, and it is difficult to maintain the temperature of the surfaces of all the samples 2 at a predetermined level during a deterioration test carried out in the apparatus 7. Accordingly, the temperatures indicated on the black panel thermometers 6 are maintained at a predetermined level, and this temperature is used as the test temperature, this indicated temperature being controlled so as to be constant by regulating the temperature of the air circulated in the test chamber 8. Therefore, in the case where the samples consist of a material the surface temperature of which increases abnormally under conditions of practical use thereof, or a material the surface of which is liable to be influenced by wind and deformed, it is difficult to easily reproduce the condition of practical use of the material in such an apparatus.

When the light fastness of a raised fiber, or a laminated compound material, such as a urethane-lined fiber or a urethane-lined vinyl, which are used as an interior finishing material for, for example, an automobile, is tested by using a conventional accelerated light fastness test machine, the deteriorated condition of the material after the accelerated test differs from the condition of the same material after a period of practical use, and test results which correlate well with the results of the practical use of the material cannot be obtained in some cases.

The above described conventional apparatus is constructed so that the temperature in the test chamber is maintained at a constant level at all times by introducing the outside air into the test chamber and circulating the outside air therein so as to maintain the temperature of the surfaces of the black panel thermometers at a predetermined level as described above. Accordingly, heat is removed from the surfaces of the samples by this introduced and circulated air, so that the temperature of the surfaces of the samples does not increase to a level which is no lower than a certain predetermined desired level. Therefore, the samples generally have a temperature gradient in which the inner portions thereof have a temperature higher than that of the surface portions thereof. On the other hand, in the conditions of practical use of this material, for example, when the material receives direct sunlight in a closed automobile, the radiation of heat from the material does not proceed sufficiently. As a result, the temperature of the material increases, and the surface temperature thereof becomes high. Accordingly, the material has a temperature gradient in which the material at a greater depth from the surface has a lower temperature. Such a temperature gradient difference is noticeable, especially, in the above-described laminated compound materials. It has been ascertained that this constitutes the main cause of the difference between the deteriorated condition of the material after a period of practical use and the deteriorated condition of the same material which has been subjected to an accelerated light fastness test. In the case of a sample the surface of which is covered with soft, raised, elongated fibers, the fibers on the surface of the material lean over and then fall due to the temperature regulating outside air introduced into and circulated in the test chamber during an accelerated light fastness test, so that the material receives the radiated light on the side surfaces of the fibers. This necessarily causes the deteriorated condition of the tested material to be different from that of the same material after a period of practical use.

The condition under which the radiated light is received and the temperature condition of a sample having a special shape and a sample of a laminated compound material are thus basically different from the conditions for the same materials in an accelerated light fastness test. It has been ascertained that this is a cause of the failure to obtain deterioration test results which correlate well with the deteriorated condition of the same material after it has been in use for a time.

OBJECT AND BRIEF SUMMARY OF THE INVENTION

It is therefore an object of the present invention to provide an improved accelerated light fastness test method for use in testing interior finishing material for vehicles, buildings and general window-surrounding surfaces, which method overcomes the problems described above.

To this end the method of the invention, in order to prevent the temperature regulating air, which is introduced into and circulated in a test chamber, from flowing in contact with the surface of a sample and taking heat away therefrom, and to prevent the light from being applied to the surface of a sample with this surface in a deformed state during an accelerated light fastness test positions a light filter over the sample while leaving a clearance of a predetermined width between the opposed surfaces of the sample and the filter so as to make the air current flowing along the surface of the sample no greater than a slight natural convection current. This makes it possible to obtain deterioration test results very close to the results after a period of practical use of the same material. It also becomes possible to vary the surface temperature of a sample while the temperature in the test chamber is kept unchanged, by varying the distance between the opposed surfaces of the sample and filter.

As a result, the correlation between the test results obtained by using the method according to the present invention and the results after a period of practical use of the tested material are greatly improved.

BRIEF DESCRIPTION OF THE DRAWINGS

The invention will not be described in greater detail in connection with the accompanying drawings, in which.

DETAILED DESCRIPTION OF THE INVENTION

Figure 1:
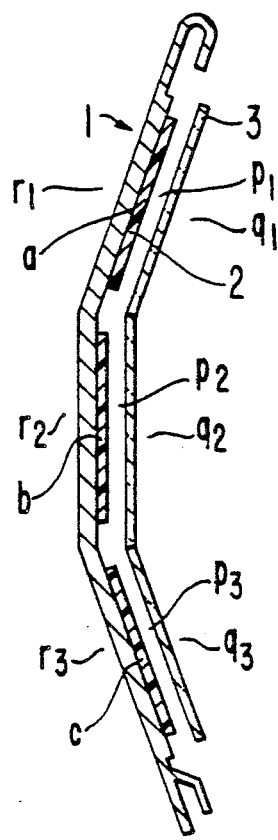
FIG. 1 is a sectional view of a sample holder used in the embodiments of the method of the present invention.
Figure 2:
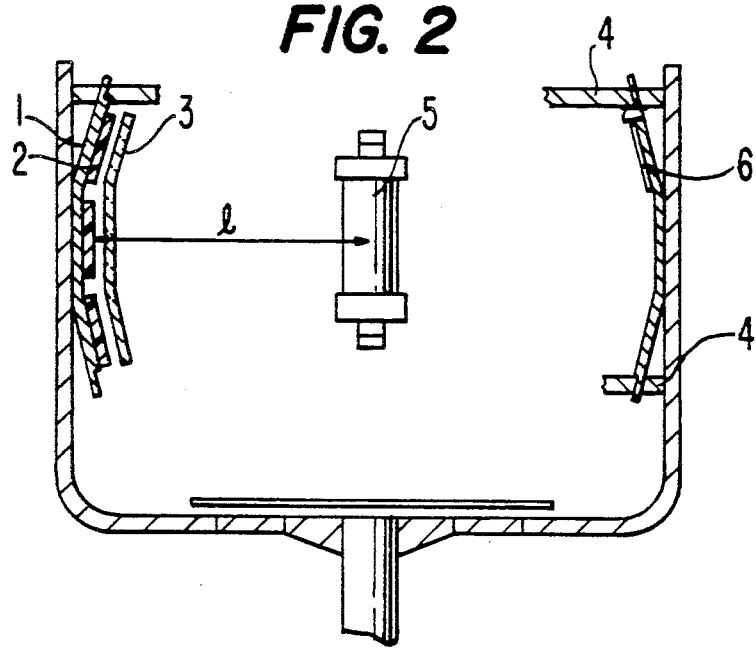
FIG. 2 is a sectional view illustrating sample support frames to which sample holders like that of FIG. 1 are secured.

FIG. 1 shows a sample holder 1 used in the test method according to the present invention, which has a light filter 3 of glass which is clear or which has a color appropriate for the test desired, and which is attached to the sample holder 1 and spaced from the face of the sample holder to leave a predetermined distance between the opposed outer surface of a sample 2 on the sample holder and the inner surface of the filter. 3. The reference letters a-c denote positions for measuring the illuminance and temperatures of the surfaces of the samples 2, p1-p3 denote the positions for measuring the air velocity in the space between the samples 2 and filter 3, q1-q3 denote the positions for measuring the air velocity in the space which is between the filter and a light source, and r1-r3 denote the positions for measuring the air velocity in the portion of the atmosphere in the test chamber which is on the opposite side of the sample holder from the light source. FIG. 2 is a sectional view of a principal portion of sample holder support frames 4 to which sample holders 1 as shown in FIG. 1 are secured, these frames 4 being arranged in an accelerated light fastness test machine as shown in FIG. 6.

Figure 6:
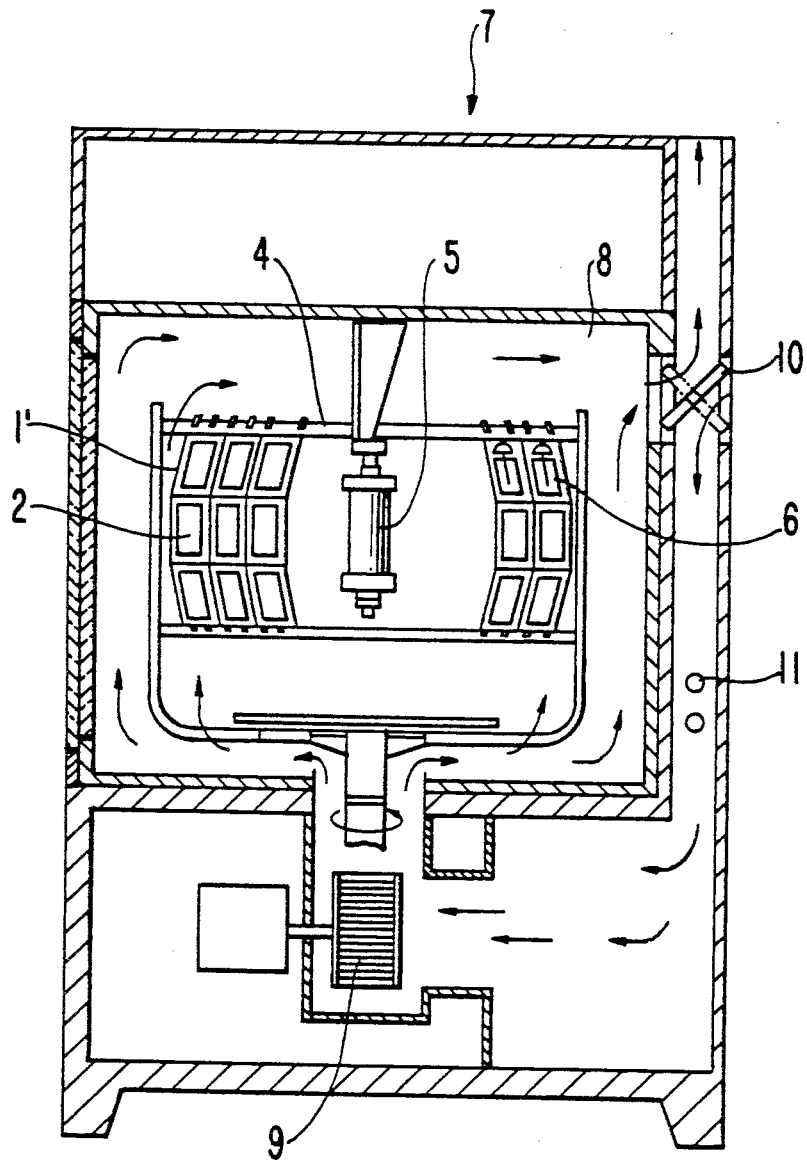
FIG. 6 is a schematic sectional side elevation of a conventional accelerated light fastness test machine.

Like samples were tested under the same temperature and light conditions in an apparatus as shown in FIG. 6.

EXAMPLE I

Referring to FIG. 1, the filter 3 was mounted so that it was spaced from the surface of the samples 2 a distance of 10 mm. A red seat material for vehicles, which had raised elongated fibers, was used as the samples 2.

The samples and filters were mounted on the sample holder frame 4 as shown in FIG. 2, and the holder frame 4 was placed in a conventional apparatus as shown in FIG. 6 and a test was conducted in which the temperature in the test chamber 8 was regulated so that the temperature on the black panel thermometer 6, which was spaced from the light source 5 at an equal distance as the distance of the surface of the sample 2 from the light source, was 90° C. with the light intensity of the light source 5 controlled so that the irradiance on the surface of the sample attained 180 W/m$^2$ at a position b in FIG. 1 in the wavelength range of 300–400 nm. The results of this test are shown in Tables 1 and 2. Table 1 shows the irradiance (W/m$^2$) and surface temperatures (°C.) in the positions a, b, c on the samples, and Table 2 shows the results of the measurements of air velocity (m/sec) in the spatial positions p1-p3, q1-q3, r1-r3 in the same test.

TABLE 1

| Item | Measuring position | | |
|---|---|---|---|
| | a | b | c |
| Irradiance (W/m$^2$) | 183.9 | 180.9 | 177.7 |
| Surface temperature (°C.) | 104.7 | 104.1 | 103.9 |

TABLE 2

| Item | | Measuring position | | |
|---|---|---|---|---|
| | | p1, q1, r1 | p2, q2, r2 | p3, q3, r3 |
| Air velocity (m/sec) | p | 0 | 0 | 0.1 |
| | q | 1.2 | 1.1 | 1.2 |
| | r | 1.3 | 1.2 | 1.2 |

As is clear from these tables, the surface temperature of the samples in the positions a, b, c in FIG. 1 were substantially 105±1° C. The air velocity in the positions q1-q3, at the front side of the filter 3 and in the positions r1-r3 at the rear side of the sample 2 was 1.1-1.3 m/sec, while the air velocity in the positions p1-p3 in the space between the surfaces of the samples 2 and the opposed surface of the filter 3 was no higher than 0–0.1 m/sec, which indicated that the air in this space was substantially currentless.

Figure 3:
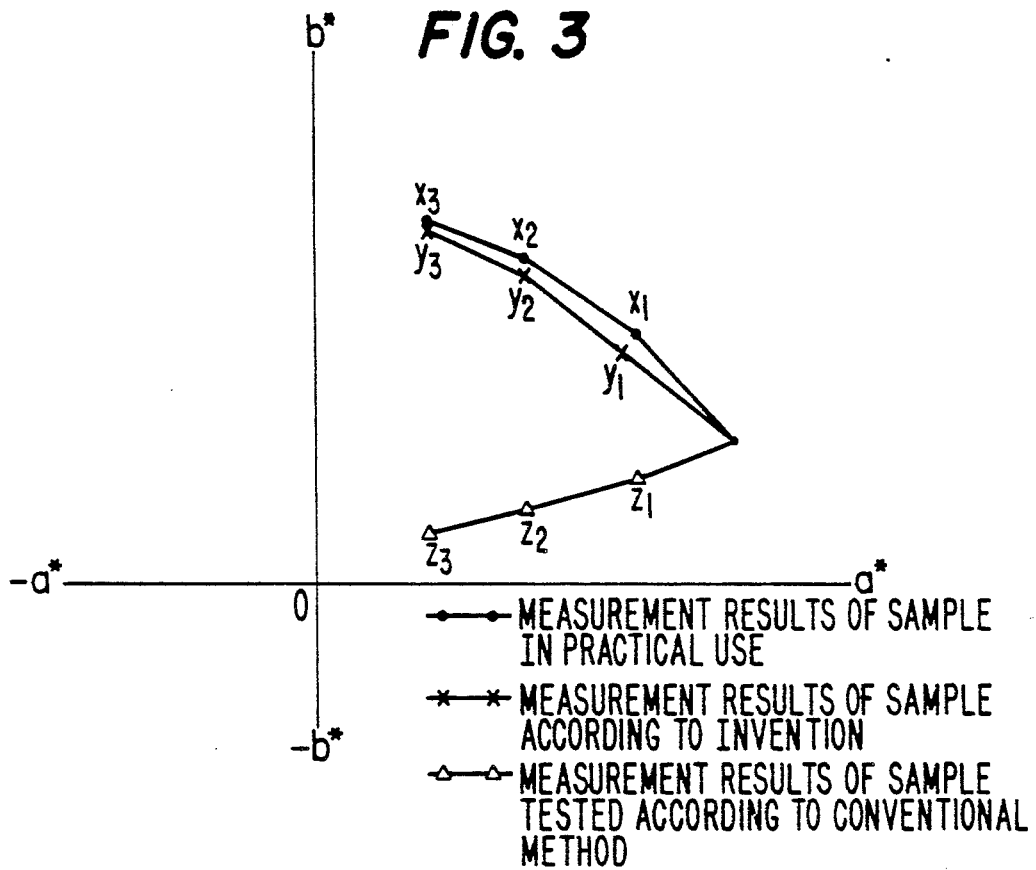
FIGS. 3, 4, 5A and 5B are graphs showing the results of experiments.
Figure 4:
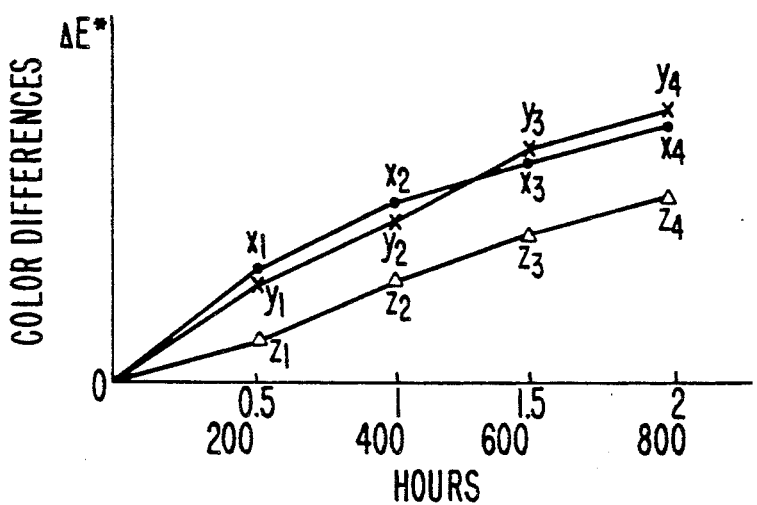

FIGS. 3 and 4 are evaluation graphs based on the results of the above tests. FIG. 3 shows the degree of deterioration of the samples on the basis of a change in color thereof. In this graph, the directivity of the change in color of the samples is shown on a CIE (L*a*b*) color specification system, in which x1-x3 represent the measurement results obtained 6 months, 12 months and 18 months after the samples 2 started being used in a practical condition of use; y1-y3 the measurement results obtained after 200 hours, 400 hours and 600 hours testing by the method according to the present invention; and z1-z3 the measurement results obtained after 200 hours, 400 hours and 600 hours testing in the conventional apparatus of FIG. 6. As will be seen from this graph, the samples used in a practical condition and those tested by the method according to the present invention were deteriorated with the color thereof "changed" from red to yellowish, while the samples tested by the conventional method were deteriorated with the red color of their surfaces simply "discolored". Therefore, it is clear that the change in color occurring on the samples tested by the method according to the present invention and that occurring on the samples used in a practical condition were well correlated with each other.

FIG. 4 shows a comparison of the deteriorated condition of the samples used in a practical condition and the deteriorated condition from accelerated deterioration of the samples tested by the method according to the present invention. What is indicated by the reference letters in FIG. 4 is similar to what is indicated by those in FIG. 3. Namely, in FIG. 4, x1–x4 represent the measurement results obtained after 6 months, 12 months, 18 months and 24 months use of the samples in a practical condition, y1–y4 the measurement results obtained after 200 hours, 400 hours, 600 hours and 800 hours testing of the samples by the method according to the present invention, and z1–z4 the measurement results obtained after 200 hours, 400 hours, 600 hours and 800 hours testing of the samples by a conventional method, these results of measurement indicating the differences ($\Delta E^*$) between the colors of the deteriorated samples and the original color thereof. Consequently, according to the method of the invention, by providing a substantially still or currentless condition of the air contacting the surfaces of the samples, accelerated deterioration tests can be conducted such that the deterioration condition of samples tested correlate well with the deteriorated condition of samples of the same material used under practical conditions, thereby improving the reliability of the accelerated deterioration test.

EXAMPLE II

Figure 5A:
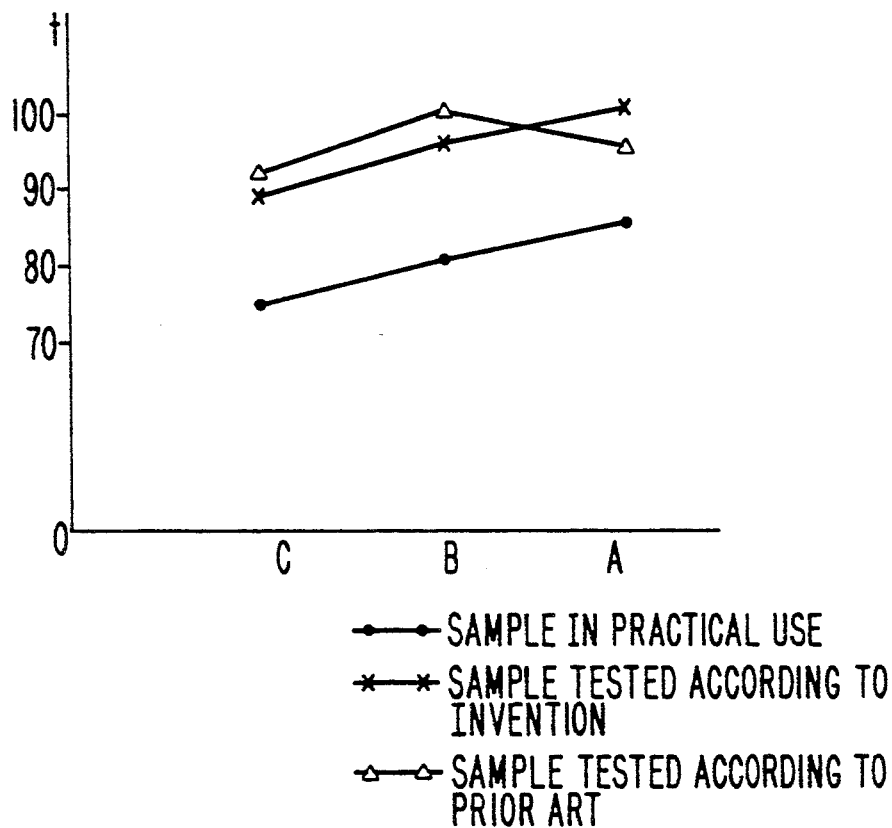
Figure 5B:
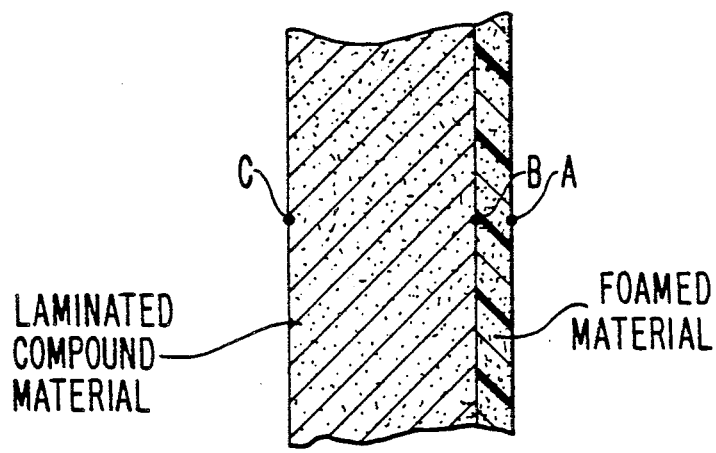

Tests were conducted under the same conditions as in Example I on a laminated compound material, which was lined with a 10 mm thick foamed urethane sheet, and which consisted of soft vinyl. FIG. 5B is a sectional view of this sample, in which the reference letters a–c denote temperature measuring points. FIG. 5A shows a graph of the results of measurement made at the points 1–3, in which the temperatures of the samples used in a practical condition, samples deteriorated by the test method according to the present invention, and samples deteriorated by a conventional test method are shown.

It will be understood from this graph that a sample tested by the method according to the present invention has a temperature gradient similar to that of a sample used in a practical condition, and in which the temperature is high at the surface of the sample and decreases the deeper into the sample the measurement is taken, and that the sample tested by the conventional method has a temperature gradient indicating that the temperature of the sample becomes higher the deeper into the sample the measurement is made. The data for the evaluation of the deterioration of the samples in this experiment was not graphed. The deterioration of the samples in this experiment actually had a tendency almost identical with that of the samples in Example I.

EXAMPLE III

A test was conducted under the same conditions as in Example I except that the same filter as was used in Example I was mounted so that the filter was spaced at 20 mm from the surfaces of the samples. The results are shown in Table 3 and 4

TABLE 3

| Item | Measuring position | | |
|---|---|---|---|
| | a | b | c |
| Surface temperature (°C.) of sample | 95.2 | 94.8 | 94.1 |

TABLE 4

| Item | | Measuring position | | |
|---|---|---|---|---|
| | | p1, q1, r1 | p2, q2, r2 | p3, q3, r3 |
| Air velocity (m/sec) | p | 0.3 | 0.3 | 0.4 |
| | q | 1.2 | 1.1 | 1.2 |
| | r | 1.3 | 1.2 | 1.2 |

The following observations can be clearly made from these tables. The air velocity in the positions q1–q3 at the front side of a filter and in the positions r1–r3 at the rear side of the filter was 1.1–1.3 m/sec which was equal to the air velocity in the corresponding positions in Example I. The air velocity p1–p3 in the space between the surfaces of samples 2 and the opposed surface of the filter 3 was 0.3–0.4 m/sec which was indicative that there was only a slight air current in this space. The surface temperature of the samples was maintained at 95±1° C. The irradiance of the light which the surfaces of the samples received was equal to that shown in Table 1, although this is not shown in Table 3. Although the deterioration accelerating capability of the method of Example III was slightly inferior to that of Example I, the test results as a whole of this Example were substantially identical with the results of Examples I and II.

EFFECT OF THE INVENTION

The method of the invention thus improves the conventional accelerated light fastness test by providing a layer of air over the irradiated surface of the sample which has at the most only a slight current. This is preferably done by positioning a light filter between the sample and the light source and spaced at a predetermined distance from the surface of the sample so that the air in the space between the surface of the sample and the opposed surface of the filter has at the most an extremely low velocity of flow. This enables the surface temperature of the sample to be maintained at a predetermined level at all times, and the deterioration of raised fibers and a laminated compound material, such as urethane-lined fiber and urethane-lined vinyl, which are used as interior finishing materials, especially, for automobiles, under practical conditions of use can be reproduced in a short period of time. The test results have excellent correlation with the results of use under natural conditions, which makes the method of the invention advantageous over conventional test methods of this kind.

I claim:

1. A method of carrying out an accelerated light fastness test on a sample of a material to be used under certain conditions of air convection along a surface thereof which is exposed to light during intended conditions of use of the material, comprising:
    positioning the sample to be tested with said surface thereof spaced at a distance from a light source having a constant intensity of light radiated therefrom for causing the said surface of the sample to receive a desired intensity of light; and
    positioning a filter between said surface of said sample and said light source at a position spaced at distance from said surface of said sample for causing air in the space between said filter and said sample to be substantially currentless, whereby the temperature conditions of the material at the surface facing the source of light are made to corresponding to the temperature conditions during the intended use of the material.

* * * * *